United States Patent [19]

Tabak et al.

[11] 4,152,363

[45] May 1, 1979

[54] VAPOR PHASE ISOMERIZATION OF METHYL-SUBSTITUTED AROMATIC HYDROCARBONS IMPROVED BY USING HIGHLY DILUTED ZEOLITE CATALYST

[75] Inventors: Samuel A. Tabak; Roger A. Morrison, both of West Deptford, N.J.

[73] Assignee: Mobil Oil Corporation, New York, N.Y.

[21] Appl. No.: 872,971

[22] Filed: Feb. 28, 1978

Related U.S. Application Data

[63] Continuation-in-part of Ser. No. 795,046, May 9, 1977, abandoned.

[51] Int. Cl.$^2$ .................... C07C 15/00; C07C 15/02
[52] U.S. Cl. .................................. 585/481; 585/488; 585/489; 252/455 Z
[58] Field of Search ............... 260/668 A, 672 T

[56] References Cited

U.S. PATENT DOCUMENTS

| | | | |
|---|---|---|---|
| 3,856,872 | 12/1974 | Morrison | 260/668 A |
| 3,856,873 | 12/1974 | Burress | 260/668 A |
| 3,887,630 | 6/1975 | Ward | 260/668 A |

*Primary Examiner*—Veronica O'Keefe
*Attorney, Agent, or Firm*—Charles A. Huggett; Raymond W. Barclay

[57] ABSTRACT

An improved vapor phase process is provided for isomerization of monocyclic methyl-substituted aromatic hydrocarbons. The process involves contacting said aromatic hydrocarbons with a catalyst material containing a crystalline aluminosilicate zeolite characterized by a silica/alumina mole ratio of at least 12 and a constraint index, hereinafter defined, within the approximate range of 1 to 12, in a reaction zone maintained under conditions such that said isomerization is accomplished in the vapor phase. The improvement resides in the catalyst being highly diluted, such as with alumina, and the reaction temperature being maintained at greater than 800° F.

23 Claims, No Drawings

VAPOR PHASE ISOMERIZATION OF METHYL-SUBSTITUTED AROMATIC HYDROCARBONS IMPROVED BY USING HIGHLY DILUTED ZEOLITE CATALYST

CROSS-REFERENCE TO RELATED APPLICATION

This is a continuation-in-part of application Ser. No. 795,046, filed May 9, 1977 now abandoned.

BACKGROUND OF THE INVENTION

1. Field of the Invention

The present invention relates to the use of specific highly diluted crystalline aluminosilicate zeolite-containing catalyst composition in a vapor phase isomerization process, said zeolite being characterized by a silica/alumina mole ratio of at least 12 and a constraint index, hereinafter defined, within the approximate range of 1 to 12, and being present in said catalyst composition at from only about 0.1 to about 5 weight percent, based on total weight of the catalyst composition.

2. Description of the Prior Art

The catalytic rearrangement of alkyl groups present in alkylaromatic hydrocarbons to provide one or more products suitable for use in the petroleum and chemical industries has heretofore been effected by a wide variety of catalysts. Acidic halides such as aluminum chloride, aluminum bromide, boron tirfluoride — hydrogen fluoride mixtures, etc. have been used in the rearrangement of alkyl benzenes to provide valuable intermediates which find utility in the synthesis of rubber, plastic, fibers and dyes. Other catalysts which have been used include solid siliceous cracking-type catalysts such as silica-alumina and clays and platinum deposited on silica-alumina. Although various catalysts possess one or more desired characteristics, a majority of catalysts heretofore employed suffer from several disadvantages. Acidic halides such as aluminum chloride, for example, are partially soluble in the feed material and are easily lost from the catalyst zone. Catalysts of this type are also uneconomical because of their extreme corrosiveness and requirement for recovery from the effluent products. Other catalysts of the heterogeneous type, such as a silica-alumina, platinum on alumina, etc., do not possess sufficient acidity to provide effective conversion and necessitate the use of relatively high temperatures above the order of 800° F. to 950° F. High temperatures frequently lead to coke formation which lowers the yield of desired product and necessitates frequent regeneration of the catalyst to remove coke. This results in reducing on-stream time and leads to high catalyst consumption due to loss of catalyst activity. Heterogeneous catalyst such as the crystalline aluminosilicates, both natural and synthetic, possess sufficient acidity but suffer the disadvantage or poor selectivity and aging as evidenced by "coke" make and the excessive amounts of disproportionated product formed in isomerization reactions.

A process in the art for isomerization of xylene is Octafining, extensively discussed in the literature as exemplified by:

1. Pitts, P. M., Connor, J. E., Leun, L. N., Ind. Eng. Chem., 47, 770 (1955).
2. Fowle, M. J., Bent, R. D., Milner, B. E., presented at the Fourth World Petroleum Congress, Rome, Italy, June 1955.
3. Ciapetta, F. G., U.S. Pat. No. 2,550,531 (1951).
4. Ciapetta, F. G., and Buck, W. H., U.S. Pat. No. 2,589,189.
5. Octafining Process, Process Issue, Petroleum Refinery, 1st Vol. 38 (1959), No. 11, Nov., p. 278.

The catalyst for use in such process is platinum on silica-alumina.

An improved catalyst for use in Octafining plants is taught by U.S. Pat. No. 3,856,872 to be of the ZSM-5 type of zeolite, whereby the process operates at high space velocities. The catalyst composition taught therein is comprised of from about 65 weight percent zeolite to about 10 weight percent zeolite.

Even in such an improved process, there is a loss of xylene presumably due to disproportionation of xylenes and transalkylation of xylenes with ethylbenzene. Metal of Group VIII of the Periodic Table of Elements is incorporated in the ZSM-5 containing catalyst primarily as a hydrogenation component that in the presence of hydrogen will inhibit coke formation and reduce aging.

U.S. Pat. No. 3,856,873 teaches vapor phase isomerization of alkylaromatic hydrocarbons in the absence of added hydrogen and over a catalyst composition containing 65 weight percent of a "ZSM-5 type" zeolite.

SUMMARY OF THE INVENTION

This invention relates to the use of an improved catalyst composition in vapor phase isomerization of monocyclic methyl-substituted aromatic hydrocarbon feed. The isomerization reaction is carried out in the presence of a catalyst composition containing a crystalline aluminosilicate zeolite characterized by a silica/alumina mole ratio of greater than 12 and a constraint index of from 1 to about 12 and a diluent such as alumina. The zeolite of the catalyst composition may contain, as replacement for at least a part of the original cations, cations of a metal of Group VIII of the Periodic Table of Elements, e.g. nickel, platinum, iron and/or cobalt, and/or hydrogen or hydrogen precursor cations. Further, the reaction temperature must be at least 800° F.

The crystalline aluminosilicate zeolites used in the catalyst composition of the process of this invention are referred to generally as ZSM-5 type or as behaving like ZSM-5 and are, for example, represented by the general formulas, expressed in terms of mole ratios of oxides in the anhydrous state, as follows:

ZSM-5

$(0.9 \pm 0.2)M_{2/n}O: Al_2O_3 : xSiO_2$ wherein M is a cation, predominately a metal of Group VIII of the Periodic Table and/or hydrogen, n is the valence of M and x is at least 5,

ZSM-11

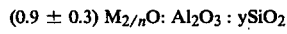
$(0.9 \pm 0.3) M_{2/n}O: Al_2O_3 : ySiO_2$ wherein M is a cation, predominately a metal of Group VIII of the Periodic Table and/or hydrogen, n is the valence of M and y is from 20 to 90,

ZSM-12

$(1.0 \pm 0.4)M_{2/n}O: Al_2O_3 : 20\text{-}200 \, SiO_2$ wherein M is a cation, predominately a metal of Group VIII of the Periodic Table and/or hydrogen and n is the valence of M, ZSM-35 and ZSM-38

$$(0.3-2.5)R_2O : (0-0.8)M_2O : Al_2O_3 : > 8\ SiO_2$$

wherein R is an organic nitrogen-containing cation derived from ethylenediamine, pyrrolidine, butanediamine or an N-methylpyridinium compound, such as the hydroxide, sulfate, nitrate or halide, for ZSM-35 and from a 2-(hydroxyalkyl) trialkylammonium compound, wherein alkyl is methyl, ethyl or a combination thereof, for ZSM-38, and M is a cation, predominately a metal of Group VIII of the Periodic Table and/or hydrogen.

DESCRIPTION OF SPECIFIC EMBODIMENTS

The catalyst composition useful in this invention contains a crystalline aluminosilicate zeolite characterized by a silica/alumina mole ratio of at least 12 and a constraint index of from about 1 to about 12, non-limiting examples of which include ZSM-5, ZSM-11, ZSM-12, ZSM-35 and ZSM-38.

Zeolite ZSM-5 is taught by U.S. Pat. No. 3,702,886, issued Nov. 14, 1972, the disclosure of which is incorporated herein by reference. In a preferred synthesized form, the zeolite ZSM-5 for use in the catalyst composition useful in this invention has a formula, in terms of mole ratios of oxides in anhydrous state, as follows:

$$(0.9 \pm 0.2)M_{2/n}O : Al_2O_3 : xSiO_2$$

wherein M is selected from the group consisting of a mixture of alkali metal cations, especially sodium, and tetraalkylammonium cations, the alkyl groups of which preferably contain 2 to 5 carbon atoms, and x is at least 5. Particularly preferred is a zeolite having the formula in the anhydrous state as follows:

$$(0.9 \pm 0.2)M_{2/n}O : Al_2O_3 : ZSiO_2$$

wherein Z is from greater than 30 to about 350 or higher.

Zeolite ZSM-11 is taught by U.S. Pat. No. 3,709,979, issued Jan. 9, 1973, the disclosure of which is incorporated herein by reference. In the as synthesized form, the zeolite ZSM-11 for use in the catalyst composition useful in this invention has a formula, in terms of mole ratios of oxides in the anhydrous state, as follows:

$$(0.9 \pm 0.3)M_{2/n}O : Al_2O_3 : 20\ to\ 90\ SiO_2$$

wherein M is a mixture of at least one of the quaternary cations of a Group V-A element of the Periodic Table and alkali metal cations, especially sodium. The original cations can be present so that the amount of quaternary metal cations is between 10 and 90 percent of the total amount of the original cations. Thus, the zeolite can be expressed by the following formula in terms of mole ratios of oxides:

$$(0.9 \pm 0.2)(xXR_4+ (1-x)M_{2/n}O) : Al_2O_3 : 20\ to\ 90\ SiO_2$$

wherein R is an alkyl or aryl group having between 1 and 7 carbon atoms, M is an alkali metal cation, X is a Group V-A element, especially a metal, and x is between 0.1 and 0.9.

Zeolite ZSM-12 is taught by U.S. Pat. No. 3,832,449, issued Aug. 27, 1974, the disclosure of which is incorporated herein by reference.

ZSM-35 is described by U.S. Pat. No. 4,016,245, the disclosure of which is incorporated herein by reference. This zeolite can be identified, in terms of mole ratios of oxides and in the anhydrous state, as follows:

$$(0.3\ to\ 2.5)R_2O : (0\ to\ 0.8)M_2O : Al_2O_3 : xSiO_2$$

wherein R is an organic nitrogen-containing cation, M is an alkali metal cation and x is greater than 8, and is characterized by a specified X-ray powder diffraction pattern.

In a preferred synthesized form, zeolite ZSM-35 has a formula, in terms of mole ratios of oxides and in the anhydrous state, as follows:

$$(0.4\ to\ 2.5)R_2O : (0\ to\ 0.6)M_2O : Al_2O_3 : ySiO_2$$

wherein R is an organic nitrogen-containing cation derived from ethylenediamine, pyrrolidine, butanediamine or an N-methylpyridinium compound, such as the hydroxide, sulfate, nitrate or halide (e.g. bromide, chloride or iodide), M is an alkali metal, especially sodium, and y is from greater than 8 to about 50.

ZSM-38 is described by U.S. Pat. No. 4,046,859, the disclosure of which is incorporated herein by reference. This zeolite can be identified, in terms of mole ratios of oxides and in the anhydrous state, as follows:

$$(0.3\ to\ 2.5)R_2O : (0\ to\ 0.8)M_2O : Al_2O_3 : xSiO_2$$

wherein R is an organic nitrogen-containing cation, x is greater than 8 and M is an alkali metal cation, and is characterized by a specified X-ray powder diffraction pattern.

In a preferred synthesized form, zeolite ZSM-38 has a formula, in terms of mole ratios of oxides and in the anhydrous state, as follows:

$$(0.4\ to\ 2.5)R_2O : (0\ to\ 0.6)M_2O : Al_2O_3 : ySiO_2$$

wherein R is an organic nitrogen-containing cation derived from a 2-(hydroxyalkyl) trialkylammonium compound, wherein alkyl is methyl, ethyl or a combination thereof, M is an alkali metal, especially sodium, and y is from greater than 8 to about 50.

Another zeolite characterized as above and, therefore, useful as a catalyst component for the present process is described in U.S. application Ser. No. 878,588, filed Jan. 17, 1978. This zeolite, possessing a definite distinguishing crystalline structure whose X-ray diffraction pattern shows substantially the significant lines set forth in U.S. Pat. No. 3,702,886 for zeolite ZSM-5, can be identified, in terms of mole ratios of oxides and in the anhydrous state, as follows:

$$(R_2O, M'_{2/n}O)_W : (Al_2O_3)_X : (SiO_2)_Y : (M''_{2/n}O)_Z$$

wherein W/X is from greater than 0.5 to less than 3, Y/X is greater than 20 and Z/X is from greater than zero to less than about 100, R is a nitrogen-containing cation and n is the valence of M' or M''. The function R may include primary amines containing 2 to 10 carbon atoms and ammonium cations, preferably the tetraalkylammonium cation in which the alkyl contains from 2 to 5 carbon atoms. The function M' is a metal from Group IA of the Periodic Table, ammonium, hydrogen or mixtures thereof. The function M'' is a metal, preferably selected from the group consisting of rare earth metals (i.e. metals having atomic numbers from 57 to 71), chromium, vanadium, molybdenum, indium, boron, mercury, tellurium, silver and one of the platinum group metals, which latter group includes platinum, palladium and ruthenium.

The original alkali metal cations of the above zeolites for use herein may be replaced, in accordance with techniques well known in the art, at least in part, by ion exchange with hydrogen or hydrogen precursor cations and metal ions of Group VIII of the Periodic Table, e.g. nickel, platinum, iron and/or cobalt.

Although the zeolites herein described have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of the zeolites for use herein is that they provide constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30.

The present invention provides a highly effective vapor phase isomerization process with a catalyst, the crystalline aluminosilicate zeolite portion of which, as suggested above, has a smaller pore size than those crystalline aluminosilicates previously used for such purpose.

The type zeolites useful in this invention freely sorb normal hexane and have a pore dimension greater than about 5 Angstroms, or, if elliptical in pore shape, at least the size of the pores in ZSM-5. In addition, the structure must provide constrained access to larger molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions. Also, structures can be conceived due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts, including those useful herein, are:

| Crystalline Aluminosilicate | CI |
| --- | --- |
| ZSM-5 | 8.3 |
| ZSM-11 | 8.7 |
| ZSM-12 | 2 |
| ZSM-35 | 2. |
| ZSM-38 | 2 |
| Beta | 0.6 |
| ZSM-4 | 0.5 |
| H-Zeolon | 0.5 |
| REY | 0.4 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The specific zeolites described, when prepared in the presence of organic cations, are catalytically inactive, possibly because the intracrystalline free space is occupied by organic cations from the forming solution. They may be activated by heating, for example, in an inert atmosphere at 1000° F. for one hour, followed by base exchange with ammonium salts and by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-35, and ZSM-38, with ZSM-5 particularly preferred.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired for the present process. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolite is associated with its high crystal anionic framework density of not less than about 1.6 grams per cubic centimeter. This high density of course must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, −11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

Members of the above group of zeolites for use in the catalyst composition of the present invention possess definite distinguishing crystalline structures as evidenced by the above U.S. Patents incorporated herein by reference.

Zeolites ZSM-5, ZSM-11, ZSM-12, ZSM-35 and ZSM-38 for use in the process of this invention are prepared as indicated in their respective patents, incorporated herein by reference above.

The zeolite described in U.S. application Ser. No. 878,588, filed Jan. 17, 1978 can be prepared utilizing materials which supply the appropriate components of the zeolite. Such components include sodium aluminate, alumina, sodium silicate, silica hydrosol, silica gel, silicic acid, sodium hydroxide and a tetrapropylammonium compound, e.g., tetrapropylammonium hydroxide. It will be understood that each component utilized in the reaction mixture for preparing the zeolite can be supplied by one or more initial reactants and they can be mixed together in any order. For example, sodium can be supplied by an aqueous solution of sodium hydroxide, or by an aqueous solution of sodium silicate; tetrapropylammonium cation can be supplied by the bromide salt. The reaction mixture can be prepared either batchwise or continuously. Crystal size and crystallization time of the composition will vary with the nature of the reaction mixture employed. It will be further understood that in the very high silica-to-alumina ratios, which can for this zeolite range from greater than 35 to about 3000 or more, and preferably from about 70 to about 500, it may not be necessary to add a source of alumina to the reaction mixture since residual amounts in other reactants may suffice.

The zeolite described in U.S. application Ser. No. 878,588, filed Jan. 17, 1978 can be prepared from a reaction mixture having a composition, in terms of mole ratios of oxides or in moles of oxides, falling within the following ranges:

| | Broad | Preferred | Most Preferred |
|---|---|---|---|
| $OH^-/SiO_2$ | 0.07–1.0 | 0.1–0.8 | 0.2–0.75 |
| $R_4N^+/(R_4N^+ + Na^+)$ | 0.2–0.95 | 0.3–0.9 | 0.4–0.9 |
| $H_2O/OH^-$ | 10–300 | 10–300 | 10–300 |
| $SiO_2/Al_2O_3$ | 50–3000 | 70–1000 | 70–500 |
| Other Metal Oxide (% of Total Oxides) | $1\times10^{-6}$–1.0 | $1\times10^{-5}$–0.1 | $1\times10^{-5}$–0.01 | wherein R is as above defined.

Typical reaction conditions for preparation of the zeolite described in U.S. application Ser. No. 878,588, filed Jan. 17, 1978 consist of heating the foregoing reaction mixture to a temperature of from about 200° F. to about 350° F. for a period of time of from about six hours to 120 days. A more preferred temperature range is from about 212° F. to about 350° F. with the amount of time at a temperature in such range being from about 12 hours to 8 days. The digestion of the gel particles is carried out until crystals form. The solid product is separated from the reaction medium, as by cooling the whole to room temperature, filtering and water washing. The foregoing product is dried, e.g. at 230° F., for from about 8 to 24 hours. Of course, milder conditions may be employed if desired, e.g. room temperature under vacuum.

For the isomerization process of this invention the suitable zeolite catalyst is employed in combination with a support or binder material which acts as diluent such as, for example, a porous inorganic oxide support or a clay binder. Non-limiting examples of such binder materials include alumina, zirconia, silica, magnesia, thoria, titania, boria and combinations thereof, generally in the form of dried inorganic oxide gels and gelatinous precipitates. Suitable clay materials include, by way of example, bentonite and kieselguhr. The relative proportion of suitable crystalline aluminosilicate zeolite of the total composition of catalyst and binder or support may vary with the zeolite content ranging from between about 0.1 to no more than about 5 percent by weight and more usually in the range of about 0.5 to about 1.5 percent by weight of the composition.

Operating conditions employed in the process of the present invention are important. Such conditions as temperature, pressure, space velocity, molar ratio of the reactants, hydrogen to hydrocarbon mole ratio, and the presence of any feedstock diluents will have important effects on the process.

The process of this invention is conducted such that isomerization of the monocyclic methyl-substituted aromatic hydrocarbon is carried out in the vapor phase by contact in a reaction zone, such as, for exmaple, a fixed bed, with catalyst under isomerization effective conditions, said catalyst being characterized as containing no more than about 5 weight percent of the above-defined zeolite which may or may not have been hydrogen or hydrogen precursor and/or Group VIII metal exchanged. This process may be conducted in either fixed or fluid bed operation with attendant benefits of either operation readily obtainable.

The present isomerization process must be carried out at a temperature between about 800° F. and about 1000° F. and at pressures ranging from about 20 psig up to about 500 psig. The weight hourly space velocities (WHSV) based on weight of total catalyst may be maintained at from about 0.5 hr$^{-1}$ to about 20 hr$^{-1}$, and the hydrogen/hydrocarbon mole ratio should be maintained at between about 1 and about 10. Within these limits the conditions of temperature and pressure will vary considerably depending upon equilibrium considerations and type of feed material. Optimum conditions are those, in which maximum yields of desired isomer products are obtained and hence considerations of temperature and pressure will vary within a range of conversion levels designed to provide the highest selectivity and maximum yield.

The starting feed materials to be employed in the present process are preferably single ring aromatic hydrocarbons containing a minimum of two and a maximum of four methyl group substituents on the ring. These feed materials may be illustrated by the following structural formula:

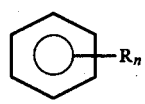

wherein R is methyl and n is an integer of 2 to 4.

Specific compounds falling within the above structural formula include para-xylene, meta-xylene, ortho-xylene, mesitylene (1,3,5-trimethylbenzene), durene (1,2,4,5-tetramethylbenzene), hemimellitene (1,2,3-trimethylbenzene), pseudocumene (1,2,4-trimethylbenzene), prehnitene (1,2,3,4-tetramethylbenzene) and isodurene (1,2,3,5-tetramethylbenzene).

Of the above listing of specific feed materials which may be used, the xylene isomers and pseudocumene are especially preferred.

As currently practiced, and in view of the prior art, vapor phase isomerization of methyl-substituted aromatic hydrocarbon feedstocks with a catalyst composition containing a zeolite as herein defined, utilizes such catalyst composition wherein the amount of active zeolite ranges from 10 to about 65 weight percent of the total catalyst composition. Employing such catalyst compositions, at temperatures within the range of 600°–700° F., allows for the following reaction characteristics:

(1) ethylbenzene conversion occurs over the catalyst acid function resulting primarily in disproportionation to benzene and diethyl benzene, (2) xylene isomerization occurs over the acid function, (3) xylenes are lost over the acid function via disproportionation to toluene and C$_9$ methyl benzenes, (4) paraffins cannot be processed because the cracked fragments will alkylate the xylenes which increases xylene loss, and (5) xylenes are lost over the acid function via alkylation with ethyl groups from ethylbenzene conversion.

The present improved process utilizes (1) a catalyst composition containing less than about 5 weight percent active zeolite, with or without metals such as platinum and nickel, with the remainder being a diluent such as alumina, with or without metals such as platinum or nickel and (2) a reaction temperature of from greater than about 800° F. to about 1000° F. At these temperatures and with the present dilute catalyst composition, ethylbenzene reacts primarily via dealkylation to benzene and ethane rather than via disproportionation to benzene and diethyl benzene and hence is strongly decoupled from the catalyst acid function. Since ethylbenzene conversion is less dependent on the acid function, a highly dilute zeolite catalyst can be used to perform the relatively easy xylene isomerization, and the amount of xylenes disproportionated is reduced. The reduction of xylene losses is important because about 75% of the xylene stream is recycled resulting in an ultimate xylene loss of 6–10 wt. %.

Since most of the ethylbenzene goes to benzene instead of benzene + diethyl benzenes, the product quality of the new process is better than the art. Moreover, since the new process utilizes less than 5% active zeolite in its catalyst compared to up to 65% active zeolite in current practice, a decrease in catalyst cost is to be expected.

The present improved process also allows greater flexibility with respect to charge stock. Since ethylbenzene conversion is relatively independent of isomerization, high ethylbenzene containing charge stocks can be processed, which means that charge stocks from thermal crackers (about 30 wt. % ethylbenzene) can be used as well as conventional stocks from reformers. In addition, dealkylation of $C_2+$ alkyl groups is favored since the temperature is greater than about 800° F. As a result, paraffins in the charge stock will not alkylate the aromatic rings, eliminating xylene loss via this mechanism. Thus, this new process can process paraffins in the charge by cracking them to lighter paraffins eliminating the need for Udex Extraction. Finally, a portion of these cracked fragments can be expected to recombine to form new aromatic rings which results in a net increase of aromatic rings. In particular, this would be true for the case where the active zeolite is diluted with a reforming type alumina with the proper metal function (e.g. platinum on alumina).

Therefore, it is hereby proposed and demonstrated that by maintaining the reaction temperature at a minimum of 800° F. and diluting the active zeolite catalyst to no more than 5 weight percent with a diluent such as alumina, improved balance between the hydrogenation activity and the acid activity of the active zeolite permits an abundance of readily noticable benefits. Those benefits include, for example, the following:

(1) use of a highly dilute (<5%) active zeolite which can be steamed or base exchanged to control acidity.

(2) decoupling of ethylbenzene conversion from xylene isomerization, (3) conversion of greater than 30 weight percent ethylbenzene charge stocks, (4) less xylene losses via disproportionation, (5) conversion of paraffin charge stocks eliminating the need for Udex extractions, (6) making benzene from ethylbenzene rather than benzene + $C_{10}$ aromatics, (7) making aromatic rings from paraffin fragments, (8) lower recycle ratios because of high ethylbenzene conversion per pass, and (9) throughput can be varied by control of the percent active zeolite in the catalyst formulation.

The specific examples, hereinafter discussed, will serve to illustrate the process of the present invention, without unduly limiting same.

EXAMPLE 1

A catalyst composition was prepared in accordance herewith which contained 0.5 weight percent zeolite ZSM-5, said zeolite containing 0.1 weight percent platinum and having a $SiO_2/Al_2O_3$ mole ratio of 70 and a CI of approximately 8.3, and 99.5 weight percent alumina. An isomerization experiment was conducted using a feedstock comprised of 10.4 weight percent ethylbenzene, 0.1 weight percent n-$C_9$ and 89.5 weight percent xylenes. The xylenes were a mixture of 73.3 weight percent m-xylene, 17.8 weight percent o-xylene and 8.9 weight percent p-xylene. The feedstock was passed over the catalyst composition at a temperature of 900° F., a pressure of 200 psig, a WHSV of 1.5 hr$^{-1}$ and a hydrogen/hydrocarbon mole ratio of 5. Product analysis at the end of 2 hours indicated 22.6 weight percent conversion of ethylbenzene and a xylene product composition of 60.16 weight percent m-xylene, 20.51 weight percent p-xylene and 19.33 weight percent o-xylene. Product analysis from this example appears in Table 3, hereinafter presented.

EXAMPLE 2

A quantity of the same catalyst composition as used in the experiment of Example 1 was used in another isomerization experiment as in Example 1 except with the WHSV maintained at 0.75 hr$^{-1}$ for 22 hours on stream. At the end of 22 hours, product analysis indicated 36.83 weight percent conversion of ethylbenzene and a xylene product composition of 56.50 weight percent m-xylene, 22.89 weight percent p-xylene and 20.61 weight percent o-xylene. Product analysis from this example appears in Table 3, hereinafter presented.

EXAMPLE 3

A catalyst composition was prepared in accordance herewith which contained 2.5 weight percent steamed HZSM-5 (the ZSM-5 having an $SiO_2/Al_2O_3$ mole ratio of 70 and a CI of approximately 8.3) and 97.5 weight percent alumina, said alumina containing 0.35 weight percent platinum. An isomerization experiment was conducted as in Example 1 except with the WHSV maintained at 10 hr$^{-1}$. After 19 hours on stream, product analysis indicated 70.96 weight percent conversion of ethylbenzene and a xylene product composition of 54.13 weight percent m-xylene, 23.30 weight percent p-xylene and 22.57 weight percent o-xylene. Product analysis from this example appears in Table 3, hereinafter presented.

EXAMPLE 4

A catalyst composition was prepared in accordance herewith which contained 1.0 weight percent HZSM-5 (the ZSM-5 having an $SiO_2/Al_2O_3$ mole ratio of 70 and a CI of approximately 8.3) and 99.0 weight percent alumina, said alumina containing 0.6 weight percent platinum. An isomerization experiment was conducted as in Example 1 except with the temperature maintained at 850° F. and the WHSV maintained at 4.4 hr$^{-1}$. The feedstock for this Example contained 29.3 weight percent ethylbenzene, 63.2 weight percent xylenes and 7.5 weight percent n-$C_9$. After 10 hours on stream, product analysis indicated 42.55 weight percent conversion of ethylbenzene and a xylene product composition of 53.71 weight percent m-xylene, 22.83 weight percent p-xylene and 23.45 weight percent o-xylene. Product analysis from this example appears in Table 3.

TABLE 3

| Product Components | Example 1 | Example 2 | Example 3 | Example 4 |
|---|---|---|---|---|
| $C_2$ | 0.60 | 1.09 | 2.10 | 2.96 |
| $C_3$ | 0.01 | 0.01 | 0.59 | 1.52 |
| $C_4$ | — | — | 0.29 | 1.45 |
| $C_5$ | — | — | 0.62 | 1.84 |
| $C_6$* | — | — | 0.18 | 0.77 |
| Benzene | 1.61 | 2.66 | 5.13 | 8.83 |
| $C_7$* | — | — | 0.02 | 0.03 |
| Toluene | 0.27 | 0.44 | 1.05 | 0.53 |
| $C_8$* | 0.01 | 0.01 | 0.23 | 0.32 |
| Ethylbenzene | 8.05 | 6.57 | 3.02 | 16.83 |
| m-Xylene | 53.20 | 49.96 | 46.70 | 33.71 |
| p-Xylene | 18.14 | 20.25 | 10.4 | 14.33 |
| o-Xylene | 17.10 | 18.22 | 19.50 | 14.72 |
| $C_9$* | 0.06 | 0.05 | — | 0.97 |
| $C_9$** | 0.53 | 0.30 | 0.31 | 0.39 |
| $C_{10}$** | 0.39 | 0.43 | 0.01 | 0.76 |
| $C_{11-12}$** | 0.03 | — | — | 0.01 |
| $C_{13}+$ | 0.02 | 0.01 | 0.03 | 0.03 |
| Xylene Loss, wt. % | 1.06 | 1.07 | 3.07 | 0.44 |

TABLE 3-continued

| Product Components | Example | | | |
|---|---|---|---|---|
| | 1 | 2 | 3 | 4 |
| Ring Loss, wt. % | 0.11 | 0.16 | 1.97 | −0.73 |

*=paraffins
**=aromatics

EXAMPLE 5

For purposes of comparison with prior art, a catalyst composition was prepared in accordance herewith which contained 65 weight percent of zeolite ZSM-5, said zeolite containing 0.8 weight percent nickel and having an $SiO_2/Al_2O_3$ mole ratio of 70 and CI of approximately 8.3, and 35 weight percent alumina. An isomerization experiment was conducted with a feedstock as in Example 1. The feedstock was passed over the catalyst composition at a temperature of 800° F., a pressure of 400 psig, a WHSV of 1.0 $hr^{-1}$ and a hydrogen/hydrocarbon mole ratio of 4.1. Product analysis at the end of 20.5 hours appears in Table 4.

TABLE 4

| Product Components | Example 5 |
|---|---|
| $C_2$ | 1.62 |
| $C_3$ | 4.20 |
| $C_4$ | 0.41 |
| $C_5$ | 0.03 |
| $C_6$* | 0.00 |
| Benzene | 4.18 |
| $C_7$* | 0.01 |
| Toluene | 26.59 |
| $C_8$* | 0.19 |
| Ethylbenzene | 0.00 |
| m-Xylene } p-Xylene | 31.42 |
| o-Xylene | 9.51 |
| $C_9$* | 0.00 |
| $C_9$** | 19.09 |
| $C_{10}$** | 1.76 |
| $C_{11-12}$** | 0.29 |
| $C_{13}+$ | 0.35 |
| Xylene Loss, wt. % | 59.07 |
| Ring Loss, wt. % | 3.79 |

*=paraffins
**=aromatics

A comparison of results obtained from the experiment of Example 5 with those from the experiments of Examples 1–4 clearly indicates the vast improvement realized by the process of the present invention over the prior art. With the prior art catalyst of Example 5, xylene loss was 59.07 weight percent as compared to a range of only 0.44 to 3.07 weight percent for the present process. Ring loss for the process conducted with the prior art catalyst was 3.79 weight percent as compared to a range of only −0.73 to 1.97 weight percent for the present process. Main products with the prior art catalyst were toluene and $C_9$ aromatics and isomerization of xylenes was small compared to disproportionation thereof.

What is claimed is:

1. In a process for effecting catalytic isomerization of monocyclic methyl-substituted aromatic hydrocarbon feedstock which comprises contacting said feedstock in the vapor phase with hydrogen at a pressure of from about 20 psig to about 500 psig, a hydrogen/hydrocarbon mole ratio of from about 1 to about 10 and a weight hourly space velocity of from about 0.5 $hr^{-1}$ to about 20 $hr^{-1}$ in the presence of a catalyst composition containing a crystalline aluminosilicate zeolite characterized by a silica/alumina mole ratio of greater than 12 and a constraint index within the approximate range of 1 to 12, the improvement wherein the amount of said zeolite in said catalyst composition is from about 0.1 to about 5 percent by weight of said catalyst composition and the reaction temperature is from about 800° F. to about 1000° F.

2. The process of claim 1 wherein said zeolite is ZSM-5, ZSM-11, ZSM-12, ZSM-35, ZSM-38 or that identified in terms of mole ratios of oxides in the anhydrous state, as follows:

$$(R_2O, M'_{2/n}O)_W : (Al_2O_3)_X : (SiO_2)_Y : (M''_{2/n}O)_Z$$

wherein W/X is from greater than 0.5 to less than 3, Y/X is greater than 20 and Z/X is from greater than zero to less than about 100, R is a nitrogen-containing cation and n is the valence of M' and M".

3. The process of claim 2 wherein said zeolite is ZSM-5.

4. The process of claim 1 wherein said zeolite is combined in an amount of from about 0.5 to about 1.5 weight percent in a binder diluent therefor.

5. The process of claim 4 wherein said binder diluent is alumina.

6. The process of claim 2 wherein said zeolite is combined in an amount of from about 0.5 to about 1.5 weight percent in a binder diluent therefor.

7. The process of claim 6 wherein said binder diluent is alumina.

8. The process of claim 1 wherein said zeolite contains cations which are predominantly hydrogen, hydrogen precursor, a metal of Group VIII of the Periodic Table of Elements or a combination thereof.

9. The process of claim 2 wherein said zeolite contains cations which are predominantly hydrogen, hydrogen precursor, a metal of Group VIII of the Periodic Table of Elements or a combination thereof.

10. The process of claim 3 wherein said zeolite contains cations which are predominantly hydrogen, hydrogen precursor, a metal of Group VIII of the Periodic Table of Elements or a combination thereof.

11. The process of claim 8 wherein said Group VIII metal cations are selected from the group consisting of nickel, platinum, iron, cobalt and mixtures thereof.

12. The process of claim 9 wherein said Group VIII metal cations are selected from the group consisting of nickel, platinum, iron, cobalt and mixtures thereof.

13. The process of claim 10 wherein said Group VIII metal cations are selected from the group consisting of nickel, platinum, iron, cobalt and mixtures thereof.

14. The process of claim 11 wherein said Group VIII metal cations are nickel or platinum.

15. The process of claim 12 wherein said Group VIII metal cations are nickel or platinum.

16. The process of claim 13 wherein said Group VIII metal cations are nickel or platinum.

17. The process of claim 1 wherein said feedstock contains materials illustrated by the formula:

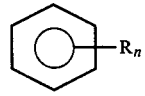

wherein R is methyl and n is an integer of from 2 to 4.

18. The process of claim 2 wherein said feedstock contains materials illustrated by the formula:

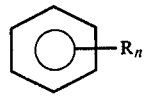

wherein R is methyl and n is an integer of from 2 to 4.

19. The process of claim 3 wherein said feedstock contains materials illustrated by the formula:

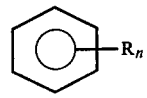

wherein R is methyl and n is an integer of from 2 to 4.

20. The process of claim 8 wherein said feedstock contains materials illustrated by the formula:

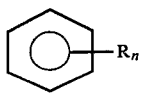

wherein R is methyl and n is an integer of from 2 to 4.

21. The process of claim 9 wherein said feedstock contains materials illustrated by the formula:

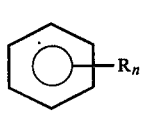

wherein R is methyl and n is an integer of from 2 to 4.

22. The process of claim 10 wherein said feedstock contains materials illustrated by the formula:

wherein R is methyl and n is an integer of from 2 to 4.

23. The process of claim 17 wherein said feedstock contains xylenes.

* * * * *

UNITED STATES PATENT AND TRADEMARK OFFICE
CERTIFICATE OF CORRECTION

PATENT NO. : 4,152,363

DATED : May 1, 1979

INVENTOR(S) : Samuel A. Tabak and Roger A. Morrison

It is certified that error appears in the above-identified patent and that said Letters Patent are hereby corrected as shown below:

Column 4, line 47, "Jan. 17, 1978" should read --February 17, 1978--.

Column 12, line 62, Table 3, under Example 3, "46.70" should read --46.79--.

Column 12, line 63, Table 3, under Example 3, "10.4" should read --20.14--.

Signed and Sealed this

Twenty-fifth Day of September 1979

[SEAL]

Attest:

LUTRELLE F. PARKER

Attesting Officer   Acting Commissioner of Patents and Trademarks